(12) United States Patent
Frampton et al.

(10) Patent No.: US 12,064,171 B2
(45) Date of Patent: *Aug. 20, 2024

(54) ELECTRICAL RETURN CONNECTIONS FOR ELECTROSURGICAL SYSTEMS

(71) Applicant: Megadyne Medical Products, Inc., Draper, UT (US)

(72) Inventors: Chad S. Frampton, American Fork, UT (US); Darcy W. Greep, Herriman, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 527 days.

This patent is subject to a terminal disclaimer.

(21) Appl. No.: 17/095,367

(22) Filed: Nov. 11, 2020

(65) Prior Publication Data

US 2021/0169572 A1 Jun. 10, 2021

Related U.S. Application Data

(60) Provisional application No. 62/944,266, filed on Dec. 5, 2019.

(51) Int. Cl.
*A61B 18/16* (2006.01)
*A61B 18/12* (2006.01)
*A61B 18/00* (2006.01)

(52) U.S. Cl.
CPC .......... *A61B 18/16* (2013.01); *A61B 18/1206* (2013.01); *A61B 2018/00077* (2013.01)

(58) Field of Classification Search
CPC ................ A61B 18/1206; A61B 18/16; A61B 2018/00077; A61B 2018/00178; A61B 2018/167; A61B 2090/0813; A61B 2017/00876

See application file for complete search history.

(56) References Cited

U.S. PATENT DOCUMENTS

| 4,166,465 A | * | 9/1979 | Esty | ........................ | A61B 18/16 607/152 |
| 2015/0306428 A1 | * | 10/2015 | Darian | ................... | A61B 90/30 601/2 |
| 2017/0365948 A1 | * | 12/2017 | Ehninger | ............... | A61B 18/16 |

FOREIGN PATENT DOCUMENTS

| EP | 1034748 | 9/2000 |
| WO | 82/00414 | 2/1982 |
| WO | 03/094766 | 11/2003 |

* cited by examiner

*Primary Examiner* — Khadijeh A Vahdat
(74) *Attorney, Agent, or Firm* — Workman Nydegger

(57) ABSTRACT

An electrosurgical system comprises a return electrode that includes a conductive element and a return conductor that forms a capacitive electrical connection with the conductive element. The conductive element is completely encompassed by one or more pads so that the conductive element is not exposed and so that the return electrode does not include an externally exposed electrical connection.

23 Claims, 9 Drawing Sheets

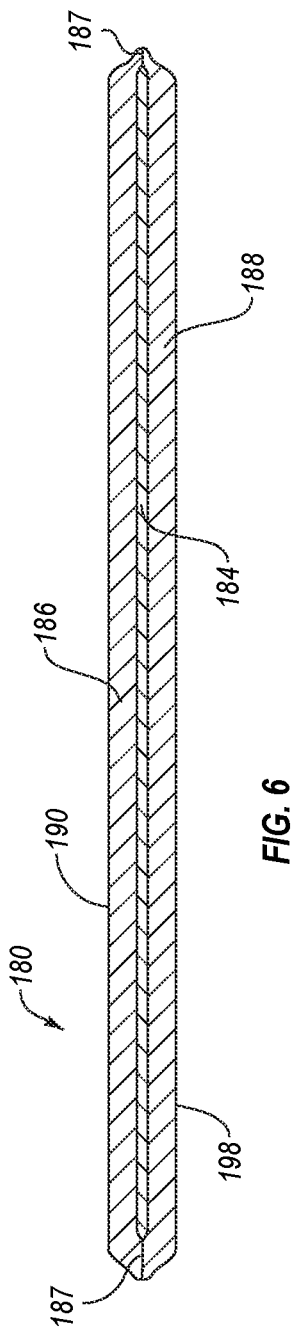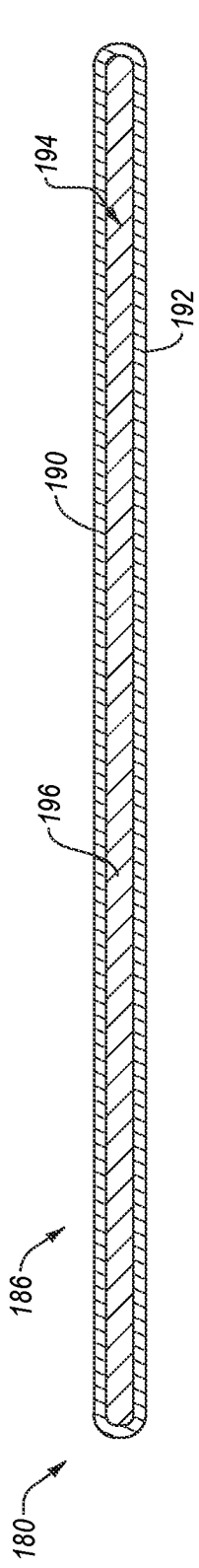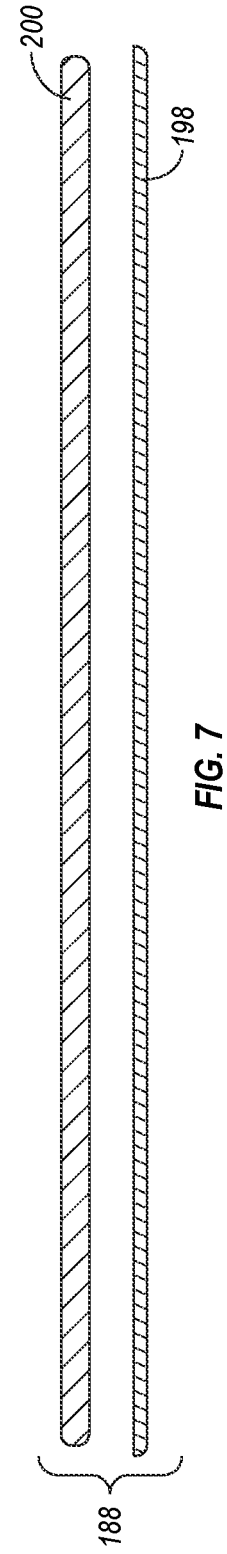

ELECTRICAL RETURN CONNECTIONS FOR ELECTROSURGICAL SYSTEMS

CROSS-REFERENCE TO RELATED APPLICATIONS

This application claims priority to and the benefit of U.S. Patent Application No. 62/944,266, filed Dec. 5, 2019, and entitled ELECTRICAL RETURN CONNECTIONS FOR ELECTROSURGICAL SYSTEMS, the entire content of which is incorporated herein by reference.

BACKGROUND

1. Technical Field

The present disclosure relates generally to electrosurgical systems. In particular, the present disclosure relates to connections for electrical return cables for electrosurgical return electrodes.

2. The Relevant Technology

In the area of electrosurgery, medical procedures of cutting tissue and/or cauterizing leaking blood vessels are performed by utilizing radio frequency (RF) electrical energy. As is known to those skilled in the medical arts, electrosurgery is widely used and offers many advantages including that of the use of a single surgical tool for both cutting and coagulation. The RF energy is produced by an RF energy source, such as a wave generator or Electro-Surgical Unit (ESU), and transmitted to a patient's tissue through a hand-held electrode that is operated by a surgeon.

Monopolar electrosurgical generator systems have an active electrode that is applied by the surgeon to the patient at the surgical site to perform surgery and a return path from the patient back to the ESU. The active electrode at the point of contact with the patient must be small in size to produce a high current density in order to produce a surgical effect of cutting or coagulating tissue. The return electrode, which carries the same current as the active electrode, has a large enough effective surface area in contact with the patient such that a low density current flows from the patient to the return electrode. An electrical return cable connected to the return electrode provides a conventional electrical return to the electrosurgical radio frequency energy source.

Since the inception of electrosurgery, various types of return electrodes have been used, including self-limiting return electrodes. Unlike typical sticky pads and steel plate return electrodes, self-limiting return electrodes are relatively large, thereby eliminating the need for conductive gels that may irritate a patient's skin. Additionally, self-limiting return electrodes typically employ geometries and materials whose impedance characteristics, at typically used electrosurgical frequencies, are such that the return electrode self-limits current densities (and corresponding temperature rises) to safe thresholds, should the contact area between the patient and the electrode be reduced below otherwise desirable levels. Furthermore, self-limiting return electrodes were specifically designed to evenly distribute the current density over the entire contact area between the patient and the return electrode in order to reduce the risk of patient burns.

Typical self-limiting return electrodes are commonly made in multiple sizes for different sized patients. For instance, a typical self-limiting return electrode for a relatively small person (e.g., under 50 lbs.) may be about 26×12 inches while a typical self-limiting return electrode for a larger person may be about 46×20 inches.

As noted above, an electrical return cable connected to the return electrode provides an electrical return to the electrosurgical radio frequency energy source. However, electrical connections between the return cable and electrode, such as conventional electrical plugs or hard-wiring present a number of issues. For example, during surgery, it is not uncommon for fluids, such as bodily fluids or other fluids used by surgeons, to be present on the operating table, and thus on the return electrode. Such fluids can flow into the connection between the return electrode and cable and short-circuit the surgical system. Thus, typical connections can provide safety hazards to the patients and medical personnel in contact with the return electrode during use. The flow of fluids into the connection can also cause damage to the surgical system. Over time, the electrical connection between the return electrode and cable may corrode or wear down until it is ineffective and in need of replacement.

In addition to the foregoing drawbacks of conventional electrical connections, electrical plugs or hard-wired connections are not adaptable to different surgical scenarios and configurations within an operating room. Often, return electrodes are configured such that a patient must lay on the return electrode in a certain orientation. The position of the connection is thus predetermined on the table, relative to the patient. However, depending on other equipment and instruments used in the operating room, and the positions taken by surgeons and other medical professionals during an operation, the placement of the connection and corresponding return cable may be inconvenient.

Furthermore, return electrodes used in the electrosurgical system that include plugs or other hard-wired connections with return cables may be cleaned and/or sterilized between patient uses. In such reusable configurations, conventional plugs and wiring connections may present recessed geometries and hard-to-reach features that may be difficult to effectively clean or disinfect using wipes or other common disinfecting techniques. The difficulty of disinfecting such plugs and connections can lead to higher risk of infection for patients and medical personnel as the return electrode is repeatedly used.

Thus, although various advances have been made in the electrosurgical arts, there remains room for improvement. More particularly, while systems and devices have been developed to increase the safety of patients undergoing electrosurgical procedures, such as by reducing the number of patient return electrode burns, the versatility and integration of return electrodes within an operating environment has remained an issue.

Therefore, it would be an advance in the present electrosurgical art to provide connection systems between return electrodes and return cables that solve the problems encountered in the art, as noted above.

BRIEF SUMMARY

The present disclosure addresses the foregoing shortcomings by providing electrical connections for use with return electrodes used in electrosurgical systems that improve safety, reduce the risk of infection, and improve operating room integration. For example, in one embodiment of the present disclosure, an electrosurgical system includes a return electrode and a return conductor. The return electrode includes a conductive element and the return conductor forms a capacitive electrical connection with the conductive element.

In one embodiment, an electrosurgical system comprises an electrical power generator, a surgical electrode connected to the electrical power generator, and a return electrode. The surgical electrode is electrically connectable to the electrical power generator and the return electrode includes a conductive element. The return electrode is configured to draw electrical current from the surgical electrode. The electrosurgical system also includes a return cable configured to carry electrical current from the return electrode to the electrical power generator or a common ground and a return conductor forming a capacitive connection between the return cable and the return electrode.

In one embodiment, an electrosurgical system includes a return electrode and a return conductor. The return electrode includes an upper pad, a lower pad, and a conductive element disposed between the upper and lower pads. The upper and lower pads extend beyond an outer perimeter of the conductive element such that the conductive element is completely encompassed by the pads. The return conductor includes a conductive plate. The return conductor is configured to be removably secured to the return electrode such that the conductive plate is capacitively connected to the conductive element of the return electrode.

In one embodiment, according to the present disclosure, an electrosurgical return electrode includes a conductive element completely encompassed by one or more pads such that no portion of the conductive element is exposed.

Additional features and advantages of the disclosed embodiments will be set forth in the description which follows, and in part will be obvious from the description, or may be learned by the practice of the disclosure. These and other features will become more fully apparent from the following description and appended claims or may be learned by the practice of the present disclosure.

BRIEF DESCRIPTION OF THE DRAWINGS

To further clarify the above and other advantages and features of the present disclosure, a more particular description will be rendered by reference to specific embodiments thereof which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIG. 6 illustrates a cross-sectional view of the return electrode illustrated in FIG. 5;

FIG. 7 illustrates an exploded view thereof;

DETAILED DESCRIPTION

The present disclosure relates generally to electrosurgical systems. In particular, the present disclosure relates to connections for electrical return cables for electrosurgical return electrodes. The return cable connections of the present disclosure improve safety by eliminating the risk of liquids disrupting the connection and short-circuiting the electrosurgical system. In addition, the connections of the present disclosure can be used with return electrodes that do not include plugs or other electrical connection features that are difficult to clean or sterilize. As such, connections of the present disclosure reduce the risk of infection from repeated use of the return electrode and return cable connection.

Furthermore, connections of the present disclosure are repositionable so that medical personnel can arrange the connection to accommodate the size or surgical needs of a patient lying on a return electrode and/or other medical systems and components within an operating room. This repositionability allows medical professionals and other medical device systems to be positioned in ideal locations for a given surgery without worrying about tripping over or unintentionally disconnecting the return cable during operations.

Figure 1:
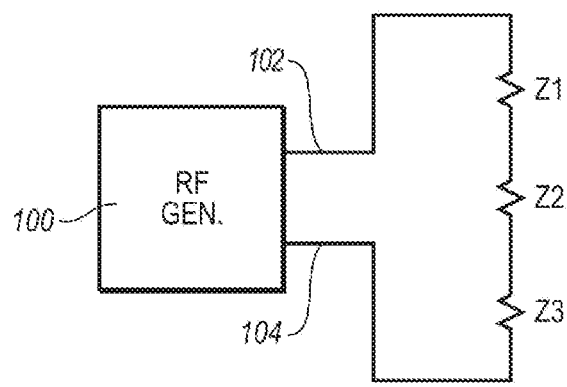
FIG. 1 illustrates an electrical schematic diagram of an embodiment of an electrosurgical system, according to the present disclosure.
Figure 2:
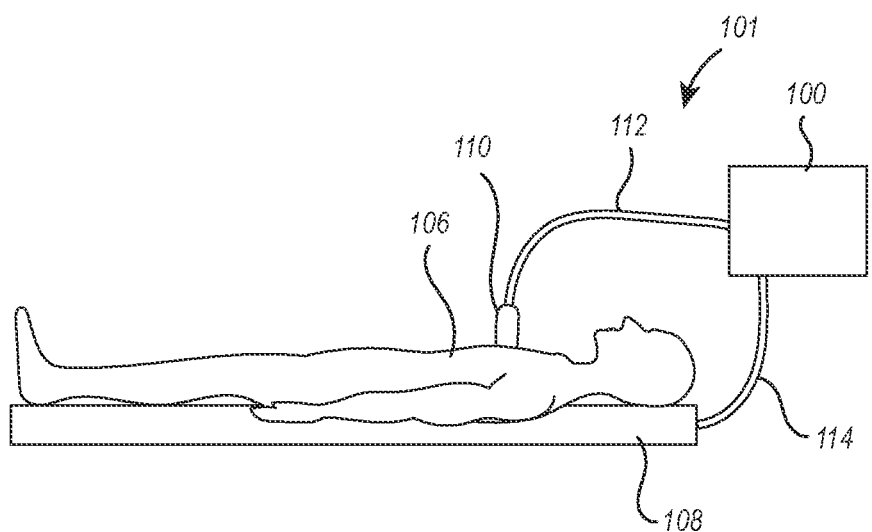
FIG. 2 illustrates an embodiment of an electrosurgical system, according to the present disclosure.
Figure 3:
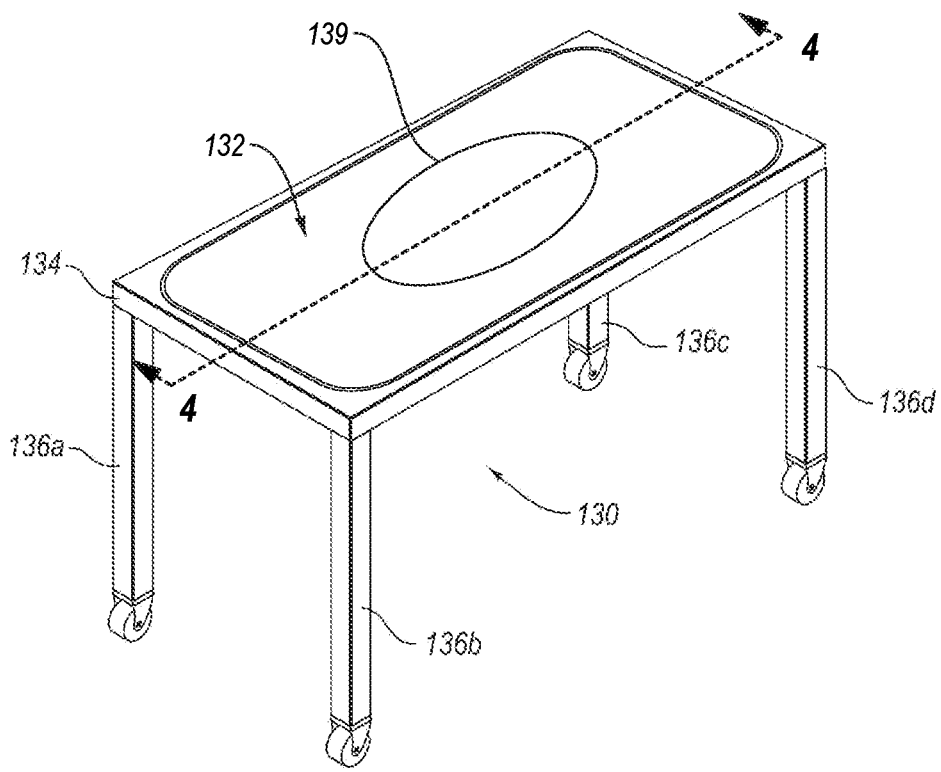
FIG. 3 illustrates an embodiment of a return electrode disposed on an operating table, according to the present disclosure.

FIGS. 1-5 and the corresponding discussion relate to the general structures and features of electrosurgical return electrodes that provide self-limiting characteristics and that can be used with patients of substantially any size. Turning to the drawings, and more particularly to FIGS. 1-3, a general discussion of self-limiting return electrodes and the general principles by which they operate will be provided. FIG. 1 thereof depicts a simplified electrical schematic diagram of an electrosurgical system illustrating typical impedances effectively included in the operative path of radio frequency current flow as presented to an electrosurgical generator during an operative procedure. There, it will be seen is conventional radio frequency electrical power generator 100, such as but not limited to constant power, voltage, and/or current or variable power, voltage and/or current generators.

Connected to electrical power generator 100 are conventional electrical conductors 102 and 104 which respectively connect generator 100 to the surgeon's implement represented by impedance $z_1$ and an electrosurgical return electrode represented by impedance $z_3$. Impedance $z_2$ is provided to represent the impedance presented by the patient's tissue lying between the operation site and the return electrode. Electrical conductors 102 and 104 are representative of one illustrative structure that is capable of performing the function of connecting means for making electrical connection to the return electrode. It may be appreciated by one skilled in the art, however, that various other structures are appropriate and capable of performing the desired function.

Although the diagram of FIG. 1 is simplified and generally considers circuit elements in terms of the principal resistances, including the reactance contributed by the surgical instrument, the patient's body and the return electrode, so as to clearly and succinctly illustrate principles of the disclosure, it should be understood that in reality certain other parameters would be encountered, parameters such as distributed inductance and distributed capacitance which, for purposes of clarity in illustration of the principles hereof, are deemed relatively small and so not considered at this point in this description.

However, as set forth below, in one embodiment when an insulating sleeve is interposed between the electrode and the body of a patient, a significant element of capacitive reactance may be included in the impedance of $z_3$. It should also be noted that the Figures are intentionally simplified so as to present the principles of the disclosure succinctly.

FIG. 2 illustrates a practical application of the electrical schematic diagram illustrated in FIG. 1 in the form of an electrosurgical system 101. In FIG. 2, a patient 106 lies on a return electrode 108 during an operation in which a hand-held surgical electrode 110 is in contact with the patient 106. The electrical power generator 100 powers the surgical electrode 110 via power cable 112. During use, current flows from the electrical power generator 100 to the surgical electrode 110 and into the patient 106. The electrical current flows through the patient 106, into the return electrode 108 and then back to the electrical power generator 100, or common ground thereof, via return cable 114.

With reference back to FIG. 1, power cable 112 of FIG. 2 is analogous to conductor 102 and return cable 114 is analogous to conductor 104. In addition, as noted above, surgical electrode 110 is represented by impedance $z_1$ of FIG. 1 and return electrode 108 is represented by impedance $z_3$. Patient 106 is represented by impedance $z_2$.

Figure 4:
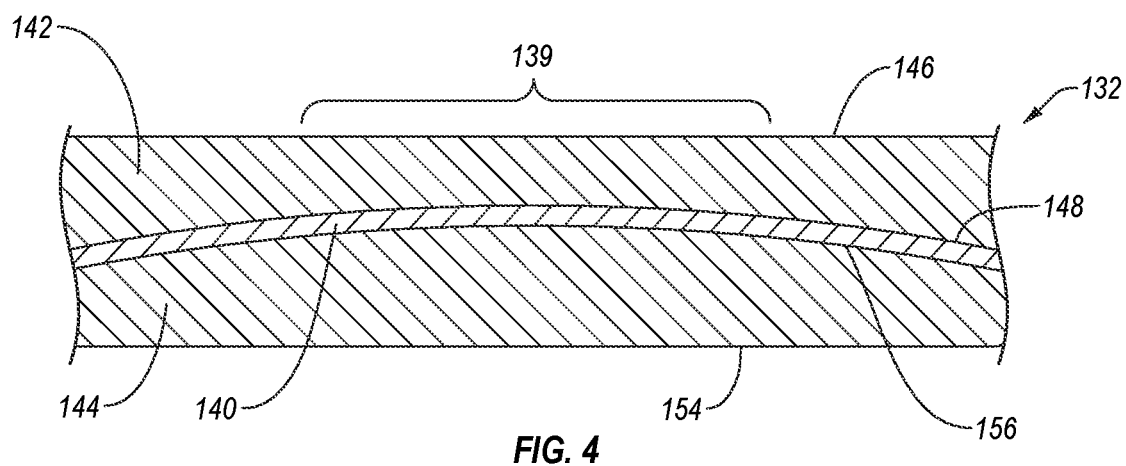
FIG. 4 illustrates a partial cross-sectional view of the return electrode illustrated in FIG. 3, according to the present disclosure.

Reference is now made to FIGS. 3-4, which illustrate an embodiment of an electrosurgical return electrode 132 according to the present disclosure. In FIG. 3, electrosurgical return electrode 132 is shown in perspective on operating table 130 with electrosurgical return electrode 132 according to the present disclosure disposed on the upper surface thereof, an edge of table 130 being identified by reference number 134. Operating table 130 is shown to have conventional legs 136a-136d that may be fitted with wheels or rollers as shown.

Table 130 is one structure that is capable of performing the function of supporting means for supporting a patient during treatment. It may be appreciated by one skilled in the art, however, that various other configurations of support means are possible and capable of performing the required function. For example, supporting means may include but not be limited to chairs, plates, beds, carts, and the like.

Although, in FIG. 3, the entire upper surface of table 130 is shown as being covered with return electrode 132, it should be understood that entire coverage is by no means required in order to practice the principles of the disclosure. Thus, when used with conventional electrosurgical generators, the return electrode needs only to present an effective working surface area which is sufficient to provide adequate resistive, capacitive, or inductive coupling at the typically employed RF frequencies so as not to interfere with the surgeon's ability to perform surgery while at the same time avoiding undesired tissue damage. It has been found that at conventional electrosurgical frequencies, this has necessitated only an effective working surface area no larger than about the projected outline of one-third of the torso for an adult patient lying on an operating table or a portion of the buttocks of a patient sitting in a chair.

However, the effective working surface area will vary depending on the material used, in some geometrical configurations, and in instances where various layers of operating room linens are placed over the electrode. The principles hereof may be successfully employed, and the effective working surface area of the return electrode determined in such circumstances, by routine experimentation. Under certain conditions, the effective working surface may be as small as about seven square inches (or about 45 square centimeters).

The surface of return electrode 132 is preferably smooth and homogeneous and includes a thin resistive and/or dielectric layer. Alternatively, the surface of return electrode 132 may include a capacitive and/or inductive layer, depending on the particular operation of return electrode 132. The characteristics of the desired dielectric for the present embodiment are sufficiently comparable to those of selected rubbers, plastics and other related materials that the latter may be satisfactorily employed as materials for the return electrode.

As mentioned above, with such a return electrode, if the patient is positioned such that not enough of the return electrode is in close proximity to the patient to result in as low impedance as needed, the results would be that the current flow from the electrosurgical generator would be reduced to a level making it difficult for the surgeon to perform surgery. Thus, in the present embodiment, notwithstanding interposition of some additional capacitance represented by a surgical gown, the features described above will continue to occur.

It will be observed that when return electrode 132 is laid out on operating table 130, the upper exposed, or working, surface of the electrode again is expansive so as to provide low impedance. Although it is not necessary that the electrode cover the entire surface of an operating table or the entire seat surface of a dental or other patient chair, it has been found advantageous in some instances to provide a greater surface area than that of the projected area of a portion of the buttocks or torso of a patient so that if a patient position shifts during the course of a procedure, a sufficient portion of the patient will remain in registration with the electrode surface so that the effective impedance will remain less than the above-described level.

FIG. 3 also illustrates that return electrode 132 includes an area 139. Area 139 of return electrode 132 may be adapted to have smaller patients positioned thereon. For instance, area 139 may be sized to have an infant sized patient positioned thereon. Furthermore, as discussed in greater detail below, return electrode 132, and particularly area 139 thereof, may be configured to provide the self-limiting characteristics discussed herein for infant sized patients positioned on area 139.

Although not illustrated, return electrode may also include additional areas configured to provide self-limiting characteristics for patients from different industry standard weight categories. By way of non-limiting example, area 139 may be configured to provide self-limiting characteristics for patients under 5 kg, a second area may be configured to provide self-limiting characteristics for patients between 5 kg and 15 kg, and a third area may be configured to provide self-limiting characteristics for patients over 15 kg. In some embodiments the areas for different sized patients may overlap one another, while in other embodiments the areas do not overlap. Furthermore, the areas may be formed concentrically with one another.

Regardless of the specific arrangement of areas for different sized patients (e.g., non-overlapping, overlapping, concentric, etc.) return electrode 132 may include one or more visual indicators to identify the areas for different sized patients. For instance, area 139 may include a visual indicator that identifies area 139 as suitable for patients under 5 kg. Similarly, a second area may include a visual indicator that identifies the second area as suitable for patients between 5 kg and 15 kg, and a third area may include a visual indicator that identifies the third area as suitable for patients over 15 kg.

The one or more visual indicators may include labels, outlines, pictures, or other indicia that are printed or otherwise displayed on the outside surface(s) of return electrode 132. The one or more visual indicators may also or alternatively take the form of color coding. For example, each area of return electrode 132 may have a different color. The colors may be printed on return electrode 132 or the colors may be integrated into other components of return electrode 132. For instance, one or more components within area 139 may have a first color while one or more components in the other area(s) may have different colors so that the areas are distinguishable from one another.

Attention is now directed to FIG. 4, which illustrates a simplified, partial section taken along the lines 4-4 of FIG. 3. As illustrated in FIG. 4, return electrode 132 includes a conductive element 140 and non-conductive or insulative pads 142, 144 on opposing sides of conductive element 140. Conductive element 140, in one configuration, is made of a conductive fabric, plastic, rubber or other flexible material.

In some embodiments, the one or more non-conductive or insulative pads 140, 142 may result in an effective DC resistance presented by each square centimeter of working surface to be greater than about 8000Ω or alternatively provide a bulk impedance of greater than 4000 Ω·cm. Various materials may be appropriate for use as the non-conductive or insulative pads 142, 144 to give the required impedance. For example, silicone, butyl rubber, or urethane have been found to be particularly attractive materials for the non-conductive or insulative pads 142, 144 as they are flexible, as well as readily washable, disinfectable, and sterilizable. Alternatively, in another embodiment, the outer pads of the return electrode may be made of an inherently relatively high resistance flexible material altered to provide the requisite conductivity. One example of the latter is that of silicone rubber material in which there are impregnated conductive fibers, such as carbon black, quantities of gold, silver, nickel, copper, steel, iron, stainless steel, brass, aluminum, or other conductors.

In some embodiments, conductive element 140 may be fabricated from a material that is substantially transparent to one or more wavelengths of electromagnetic radiation, such as but not limited to, microwave radiation, infra-red (IR) radiation, ultraviolet (UV) radiation, X-ray radiation, radio frequency (RF), and the like. This allows conductive element 140 and return electrode 132, when the other components of return electrode 132 are transparent to one or more wavelengths of electromagnetic radiation, to be maintained in place during performance of certain medical procedures using particular wavelengths of electromagnetic radiation.

It may be appreciated by one skilled in the art that conductive element 140 may have various other configurations so long as conductive element 140 is capable of performing the functions of an electrode, i.e., being capable of passing current therethrough. For example, in some embodiments, conductive element 140 includes a thin, highly conductive lower stratum that facilitates connection of return electrode 132 to an electrosurgical radio frequency energy source (not shown). In another alternate embodiment, conductive element 140 is configured from multiple layers of conductors. In still yet another embodiment, conductive element 140 includes an outer dielectric layer that substantially surrounds an interior-conducting layer, similar to the self-limiting electrosurgical electrodes described previously.

Referring still to FIG. 4, disposed on opposing sides of conductive element 140 are pads 142, 144. As can be seen, pad 142 has an outer surface 146 and an inner surface 148. Outer surface 146 is configured to be placed against the surface of a patient (thereby acting as a working surface of return electrode 132), while inner surface 148 is disposed next to conductive element 140. In some embodiments, inner surface 148 is secured to conductive element 140, such as with an adhesive, to prevent air bubbles or separation between pad 142 and conductive element 140. Pad 142 may include outer and inner cover layers that are formed individually and secured together about their edges or are integrally formed. The outer and inner cover layers may define outer and inner surfaces 146, 148. Outer and inner cover layers may be formed of various materials, such as urethane, polyurethane, polyethylene, polypropylene, polyolefins, polyvinyl chloride, PET, etc. A fill material, discussed below, may be disposed between the outer and inner cover layers.

Similar to pad 142, pad 144 includes an outer surface 154 and an inner surface 156. Outer surface 154 is configured to be placed on a support surface (e.g., operating table, chair, etc.), while inner surface 156 is disposed next to conductive element 140. Like outer and inner cover layers 146, 148, one or both of outer surface 154 and inner surface 156 may be defined by a cover layer formed of various materials, such as urethane, polyurethane, polyethylene, polypropylene, polyolefins, polyvinyl chloride, PET, etc. Like pad 142, inner surface 156 may be secured to conductive element 140, such as with an adhesive, to prevent air bubbles or separation between pad 144 and conductive element 140. In other embodiments, however, the edges of pad 144 may be secured to the edges of pad 142 with conductive element 140 disposed therebetween. Also, like pad 142, pad 144 may include a fill material.

Fill materials used in pads 142, 144 may provide return electrode 132 with some pressure reducing characteristics. More specifically, since pads 142, 144 retain a defined volume of fill material, when an individual rests upon return electrode 132, the fill materials distribute the downward force of the patient throughout the fill materials, thereby decreasing the point forces applied to those parts of the patient's anatomy where bony prominences or other areas of increased pressure are located. Nevertheless, as discussed elsewhere herein, pads 142, 144 are relatively thin to ensure sufficient coupling between a patient and conductive element 140. Accordingly, in some situations, such as during lengthy surgical procedures, it may be desirable or necessary to use a separate pressure reducing pad in combination with return electrode 132 to prevent the formation of pressure sores on the patient or to increase the patient's comfort level.

Fill materials used in pads 142, 144 may act as dielectric layers to reduce the current that flows through pads 142, 144, respectively. Alternatively, the fill materials may take the form of conducting materials to aid with the transmission of current therethrough. Additionally, the fill materials may provide a thermal mass for the distribution of heat during an electrosurgical procedure. As discussed above, IEC requires that during an electrosurgical procedure the temperature rise of the patient's tissue should remain below six degrees Celsius (6° C.). The thermal mass provided by the fill materials assists with the distribution of heat throughout the patient's body and substantially eliminates, in combination with the self-limiting characteristics of return electrode 132, the potential for hot spots that may burn the patient. Consequently, the substances used for fill materials may perform multiple functions during an electrosurgical procedure.

In general, the fill materials may take the form of one or more solids, liquids, gases, or combinations thereof depending on the pressure reducing, dielectric, and/or conducting properties needed for return electrode 132. For example, in one illustrative embodiment, the fill materials are elastomeric gels having low durometer level, such as SORBOTHANE. In addition to SORBOTHANE, various other elastomeric gels may be used, such as but not limited to those based upon the polymer chemistry of urethanes, silicones, hydrophilic elastomers or hydrogels, vinyls, vinyl alcohols, or other similar materials and technologies. Additionally, the fill materials may take the form of water, saline, water-based materials, conductive oils, and the like. Still further, the fill materials may take the form of solid but flexible foam-type materials.

The materials forming return electrode 132, conductive element 140, and pads 142, 144, at least partially control the passage of current from a patient to conductive element 140. As such, in one embodiment, pads 142, 144 are insulative. In an alternate configuration, pads 142, 144 may be conductive and aid in the passage of current from the patient to conductive element 140. So long as the return electrode 132 provides the self-limiting characteristics described herein, the various elements of return electrode 132, i.e., conductive element 140 and pads 142, 144, may provide one or more resistive, inductive, and/or capacitive inductance components to the bulk impedance of the return electrode. In this manner return electrode 132 is self-limiting, while also providing at least some pressure reducing characteristics.

In addition to the materials used to form pads 142, 144, the thickness and arrangement of pads 142, 144 and conductive element 140 can affect the transmission of current from a patient to conductive element 140. By way of non-limiting example, the distance between outer surface 146 of pad 142 and conductive element 140 can affect the capacitive coupling between conductive element 140 and a patient resting upon return electrode 132. Through this capacitive coupling, current used during electrosurgery is passed from the patient to return electrode 132. As will be understood by one of ordinary skill in the art in light of the disclosure herein, the capacitive coupling between the patient and return electrode 132 can be directly related to the self-limiting characteristics of return electrode 132. Thus, by changing the distance between the outer surface 146 and the conductive element 140, the capacitive coupling between the patient and the return electrode 132 can be adjusted.

Note that the return electrode 132 shown in FIG. 3 does not include a conventional electrical connection, such as a hard-wired connection or plug anywhere on the return electrode 132. The various embodiments of return electrodes 132 described herein are configured such that no external plug or hard-wired electrical connection is necessary. Advantageously, such configurations allow medical personnel to arrange and position the return electrode 132 anywhere within an operating room, regardless of where an electrical outlet or other power source, such as the electrical power generator 100, may be located.

For example, with traditional return electrodes having external plugs or other hard-wired, exposed conductive connections, the return electrode plug must be situated within the operating room in a convenient position relative to the energy source, such that a conductive cord can reach between the energy source and the return electrode plug without obstructing medical personnel or other medical system during an operation. Thus, external plugs and other hard-wired conductive connections limit the orientations available when setting up the return electrode on an operating table for patient use. The available orientations of return electrodes having external plugs are further limited by the presence of other medical devices and systems connected to the patient, positioned around the operating table, or being used by a doctor or nurse, which conductive cords and energy sources must also accommodate.

In addition to integrating return electrodes having external plugs into existing operating rooms having other devices and systems, other factors further complicate the integration and use of return electrodes having external plugs or other hard-wired conductive connections. For example, medical personnel must take precautions to orient return electrodes having external plugs so that the plug is not in contact with the patient during use, which could cause electrical current to flow back into the patient, causing injury and reducing the effectiveness of the surgical system. Also, for example, medical personnel must take precautions so that the position of the external plug minimizes the chance of fluids entering the plug and disrupting the electrical circuit of the surgical system. All of these factors make it difficult to ensure safe and convenient use of return electrodes having external plugs.

Figure 5:
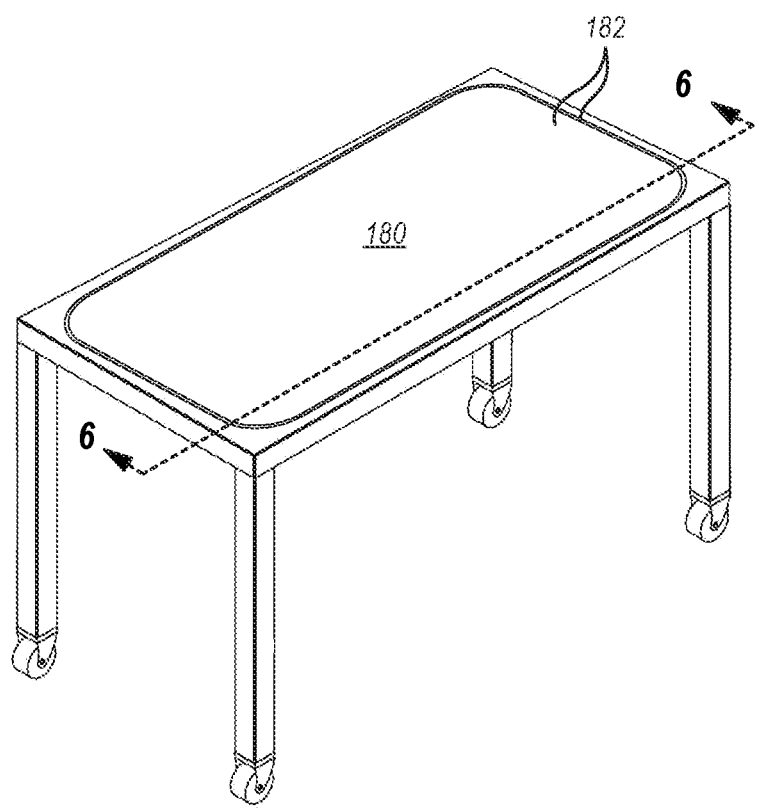
FIG. 5 illustrates an embodiment of a return electrode on an operating table, according to an embodiment of the present disclosure.

In contrast, and advantageously, return electrodes 132 of the present disclosure eliminate the various complications presented by external electrical plugs and other exposed conductive connections by eliminating any external plugs altogether. That is, as shown in FIGS. 3 and 5, as well as subsequent figures described herein, the return electrode 132, 180 includes no such external plugs. Rather, the return electrodes 132, 180 of the present disclosure can be oriented and arranged in any configuration within an operating room and underneath a patient without moving the position of the electrical connection between the conductive element 140 and a return cable 114. In order to accomplish the foregoing, at least one embodiment of an electrosurgical system comprises a reconfigurable capacitive electrical connection between the conductive element 140 of the return electrode 132, 180 and the return cable 114. The capacitive connection can occur anywhere on the return electrode regardless of the position and orientation of the return electrode 132, 180 on the operating table, in an operating room, or relative to a patient.

More detail regarding various embodiments of such capacitive connections and apparatus will be given hereafter but first attention is directed to FIGS. 5-7, which illustrate an electrosurgical return electrode 180 without externally exposed electrical plugs, according to an embodiment of the present disclosure. FIG. 5 illustrates return electrode 180 on operating table 130. Similar to return electrode 132, return electrode 180 does not include an exposed electrical connection to provide a conventional electrical return to the electrosurgical radio frequency energy source. Rather, in at least one embodiment, the outer layers 182 of the return electrode 180 completely encompass a conductive element disposed completely within the return electrode 180 so that no portion of the conductive element is accessible from outside the return electrode 180.

In such an embodiment, the return electrode 180 includes a simplified geometry without hard-to-reach contours and recesses of an externally exposed electrical plug or other common conductive connection. This is advantageous when cleaning and/or sterilizing the return electrode 180 between patient uses to reduce the risk of infections. For example, typical return electrodes include a conductive connection or plug in communication with the conductive element inside the return electrode. During sterilization with wipes or other common sterilization techniques, it is difficult for medical personnel to reach the inside contours and crevasses of the electrical connection. As such, bacteria is prone to remain within the connection. In contrast, the return electrodes 132, 180 of the present disclosure do not include such common connections. As a result, the return electrode 180 can more easily be thoroughly wiped and sterilized between uses, reducing risk of infection to the patients laying thereon.

In addition, the material of the conductive element inside the return electrode 180 is not exposed in any way to be corroded, damaged, or otherwise harmed when shipped, moved, stored, and used. No electrical connection is present to break or corrode. Also, the return electrode may be freely folded, rolled, or otherwise packaged and stored in any number of ways without rigid or bulky electrical connections getting in the way or complicating packaging or storing processes.

To illustrate the construction of at least one embodiment of the return electrode 180, including the conductive element disposed therein, FIG. 6 illustrates a simplified section taken along the lines 6-6 of FIG. 5 and FIG. 7 illustrates an exploded view of return electrode 180. As illustrated in FIGS. 6 and 7, return electrode 180 includes a conductive element 184 and pads 186, 188 on opposing sides of conductive element 184. Pads 186, 188 may be referred to individually as upper pad 186 and lower pad 188. However, as will be clear from subsequent descriptions and figures, either pad 186, 188 may be oriented above or below the conductive element 140 during use while maintaining the functionality of the return electrode 180. Indeed, at least one advantage of the return electrode 180 is that medical personnel can place the return electrode 180 in any orientation on the operating table 130 without losing functionality provided by the return electrode. That is, the return electrode 180 may be placed on the operating table 130 with either pad 186 or pad 188 facing up and upon which a patient may rest.

Conductive element 184, in one configuration, may be similar to conductive element 140. Nevertheless, it may be appreciated by one skilled in the art that conductive element 184 may have various other configurations so long as conductive element 184 is capable of performing the functions of an electrode, i.e., being capable of passing current therethrough.

Referring still to FIGS. 6 and 7, disposed on opposing sides of conductive element 184 are pads 186, 188. As can be seen, pad 186 has an outer cover layer 190 and an inner cover layer 192 that define an interior chamber 194 therebetween. Outer cover layer 190 is configured to be placed against the surface of a patient (thereby acting as a working surface of return electrode 180), while inner cover layer 192 is disposed next to conductive element 184. In some embodiments, inner cover layer 192 is secured to conductive element 184, such as with an adhesive, to prevent air bubbles or separation between pad 186 and conductive element 184. Outer and inner cover layers 190, 192 may be formed individually and secured together about their edges or may be integrally formed. Outer and inner cover layers 190, 192 may be formed of various materials, such as urethane, polyurethane, polyethylene, polypropylene, polyolefins, polyvinyl chloride, PET, etc. A fill material 196, similar to that discussed elsewhere herein, may be disposed in interior chamber 194.

Similar to pad 186, pad 188 includes an outer cover layer 198 and a fill material 200. Outer cover layer 198 is configured to be placed against the surface of a patient (thereby acting as a second working surface of return electrode 180), while fill material 200 is disposed next to conductive element 184. Like outer and inner cover layers 190, 192, outer cover layer 198 may be formed of various materials, such as urethane, polyurethane, polyethylene, polypropylene, polyolefins, polyvinyl chloride, PET, etc.

Rather than having a second inner cover layer, pad 188 may be formed during the assembly of return electrode 180. For instance, during assembly of return electrode 180, chamber 194 in pad 186 may be filled with material 196 and sealed closed such that material 196 cannot escape from chamber 194. Pad 186 may be disposed next to and/or secured to a first major surface of conductive element 184. The edges of outer cover layer 198 may then be secured to the edges of pad 186 so as to create a chamber between conductive element 184 and outer cover layer 198. The newly defined chamber may then be filled with material 200 and sealed closed to retain material 200 therein.

It will be appreciated that pads 186, 188 may be similar or identical to one another. For instance, in addition to outer cover layer 198 and material 200, pad 188 may also include an inner cover layer (similar to inner cover layer 192) that cooperates with outer cover layer 198 to define a chamber for receiving material 200. Furthermore, pad 188 may also be at least partially secured to conductive element 184. For instance, in embodiments where pad 188 includes an inner cover layer, the inner cover layer may be secured, such as with an adhesive, to a second major surface of conductive element 184.

Likewise, pad 186 may be similar to pad 188 in that pad 186 may be formed without inner cover layer 192. In such an embodiment, the outer layer 190 of pad 186 may be secured to outer layer 198 of pad 188. Additionally, or alternatively, in at least one embodiment, each outer layer 190, 198 may at least partially secure to the conductive element 184, for example at an outer edge thereof, as well as to the opposing outer layer 190, 198.

In any case, one will appreciate that the conductive element 184 of the return electrode 180 is completely encompassed by the surrounding pads 186, 188 so that the conductive element 184 is not exteriorly exposed in any way, as shown in the embodiments of return electrodes 132, 180 illustrated in FIGS. 3 and 5.

While FIG. 6 illustrates a cross-sectional view of the return electrode 180 taken along lines 6-6 in FIG. 5, the cross-sectional view of the return electrode 180 would look similar regardless of the orientation of the line 6-6, whether it be longitudinal, lateral, or diagonally disposed across the return electrode 180. That is, the pads 186, 188 extend beyond the outer edges of the conductive element 184 around the entire perimeter of the return electrode 180 so that the conductive element is disposed within, and completely encompassed by, the pads 186, 188.

In at least one embodiment, the pads 186, 188 are welded, adhered, sealed, or otherwise formed together at a pad juncture 187 around the outer perimeter of the conductive element 140. In at least one embodiment, the pads 186, 188 are integrally formed together as a single piece. In any case, as noted above, the conductive element 184 is completely surrounded and encompassed by the pads 186, 188 so that no portion of the conductive element 184 is exposed or extending beyond the pads 186, 188. Furthermore, as noted above with reference to FIG. 3, there is no conductive electrical plug or any other external conductive electrical connection that passes through the pad juncture 187 at any point around the perimeter of the return electrode 180 to make conductive electrical contact with the conductive element 184. The conductive element 184 is thus completely isolated from the environment outside of the pads 186, 188.

The materials forming return electrode 180, conductive element 184, and pads 186, 188, control the passage of current from a patient to conductive element 184. As such, in one embodiment, pads 186, 188 and fill materials 196, 200 are insulative, while, in an alternate configuration, pads 186, 188 and/or materials 196, 200 may be conductive and aid in the passage of current from the patient to conductive element 184. So long as return electrode 180 provides the self-limiting characteristics described herein, the various elements of return electrode 180, i.e., conductive element 184 and pads 186, 188, may provide one or more resistive, inductive, and/or capacitive inductance components to the bulk impedance.

In addition to the materials used to form pads 186, 188, the thickness of pads 186, 188 can affect the transmission of current from a patient to conductive element 184. By way of non-limiting example, forming pads 186, 188 relatively thin can facilitate capacitive coupling between conductive element 184 and a patient resting upon return electrode 180. Through this capacitive coupling, current used during electrosurgery is passed from the patient to return electrode 180. As will be understood by one of ordinary skill in the art in light of the present disclosure, the capacitive coupling between the patient and return electrode 180 can be directly related to the self-limiting characteristics of return electrode 180. Thus, making pads 186, 188 relatively thin contributes to good electrical coupling between the patient and return electrode 180 so as to enable safe and effective electrosurgery for substantially any sized patient. Accordingly, one or both of pads 186, 188 may have a thickness within a predetermined range.

For instance, in some embodiments, one or both of pads 186, 188 has an approximate thickness of between about 0.02 inches and about 0.120 inches. In other embodiments, one or both of pads 186, 188 has an approximate thickness of less than about 0.10 inches, about 0.09 inches, about 0.075 inches, about 0.06 inches, about 0.05 inches, about 0.03 inches, or about 0.02 inches. In some embodiments, return electrode 180 has a total thickness of about 0.135 inches or less.

The inclusion of pads 186, 188, which are substantially similar to one another, on opposing sides of conductive element 184 provides return electrode 180 with a substantially symmetrical construction. The symmetrical nature of return electrode 180 provides return electrode 180 with two surfaces that function as working surfaces. More specifically, the major surfaces of return electrode 180 defined by outer cover layers 190, 198 may each be used as a working surface. For instance, return electrode may be positioned so that outer cover layer 192 is positioned towards a patient and return electrode 180 will exhibit the self-limiting characteristics discussed herein. Likewise, return electrode 180 can be turned over so that outer cover layer 198 is positioned against a patient and return electrode 180 will exhibit the self-limiting characteristics discussed herein.

As noted above with reference to FIG. 2, a return cable 114 may be connected to the return electrode 180 to carry electrical current back to the electrical power generator 100, thus drawing current out from the patient via the return electrode 180. Accordingly, electrosurgical systems incorporating the various embodiments of return electrodes 132, 180 described herein may employ one or more capacitive electrical connections that allow current to be induced by capacitive coupling across the pads 186, 188 surrounding the conductive element 184, or any other materials separating the conductive element 184 from the return cable 114.

Figure 8:
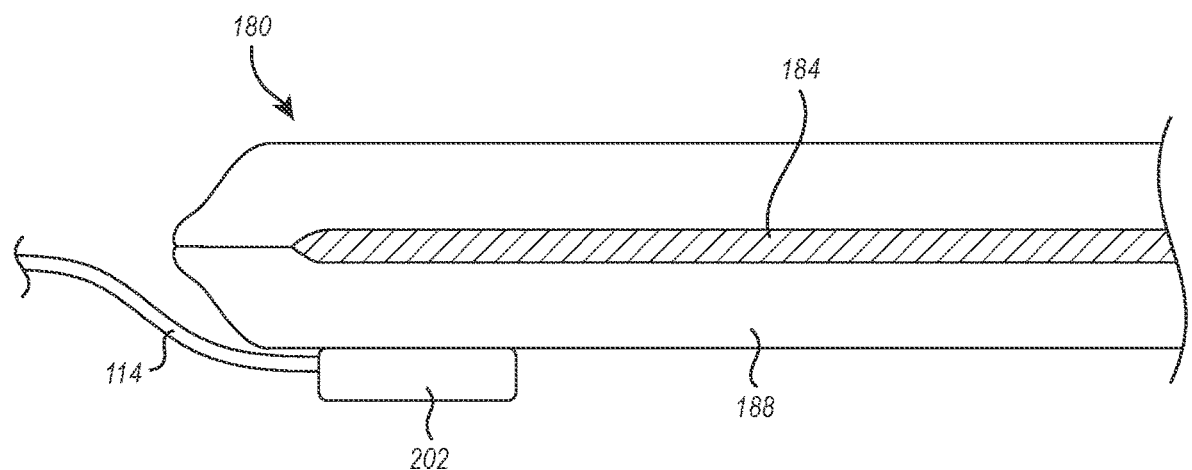
FIG. 8 illustrates an embodiment of a return conductor forming a capacitive connection with a return electrode, according to the present disclosure.

For example, as shown in FIG. 8, a return conductor 202 may be placed against the lower pad 188 of return electrode 180 such that it is brought into close enough proximity to the conductive element 184 of the return electrode 180 to form a capacitive connection therebetween. The return conductor 202 may be connected to the lower pad 188 so that current in conductive element 184 induces current in the return conductor 202, which flows to the electrical power generator 100 via the return cable 114, which is connected to the return conductor 202.

One will appreciate that the materials separating the conductive element 184 of the return electrode 180 and the return conductor 202 may vary between embodiments described herein and will affect the inducement of current by the conductive element 184 in the return conductor 202. In addition, some materials, as well as the thicknesses of material layers between conductive elements 184, 202 may present unique properties that operate as dielectric materials between the conductive element 184 and return conductor 202.

Such materials and thicknesses described herein may present unique filtering effects, such as high-frequency, low-frequency, or band-pass filtering of frequencies generated by the electrical power generator 100 for use with the hand-held surgical electrode 110. Because the frequencies used during an operation may vary depending on the type of operation and/or specific electrode used, the materials separating the conductive element 184 and return conductor 202 can be specifically designed to provide sufficient capacitive coupling and current generation by conductive element 184 in return conductor 202.

In some embodiments, materials separating the conductive element 184 and return conductor 202 may include, for example, materials coating or surrounding the exterior conductive element 202.

The various embodiments of return conductors 202 described herein, including the return conductor illustrated in FIG. 8 and subsequent figures, are configured to be removably secured to a return electrode, such as the return electrodes 132, 180 illustrated in FIGS. 3 and 5 and other return electrodes described herein. When secured thereto, the return conductor 202 forms a capacitive electrical connection between the return electrode 180 and the return cable 114. However, the various embodiments of return conductors described herein can be easily removed and re-secured or repositioned on the return electrode 180 prior to, during, or after use. As such, the removable return conductors of the present disclosure are reconfigurable to allow any number of orientations of the return electrode 180 within an operating room on the operating table 130 while still enabling the necessary capacitive connection required for current generation by the return electrode 180 in the return conductor 202, which is then carried by the return cable 114 to the electrical power generator 101.

Figure 9A:
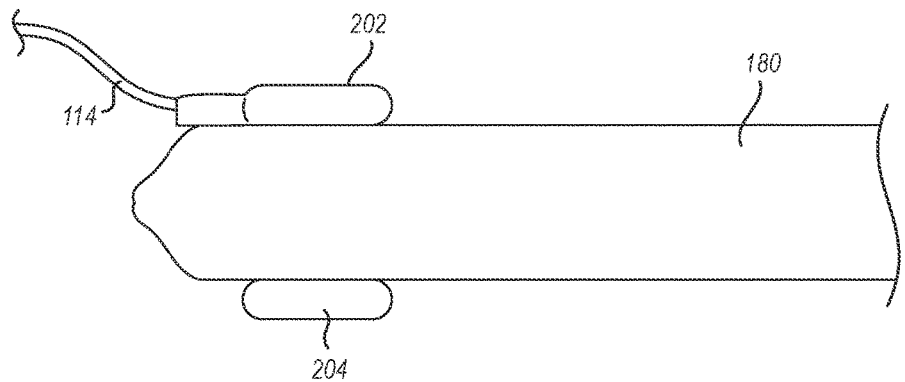
FIG. 9A illustrates an embodiment of a return conductor forming a capacitive connection with a return electrode, according to the present disclosure.
Figure 9B:
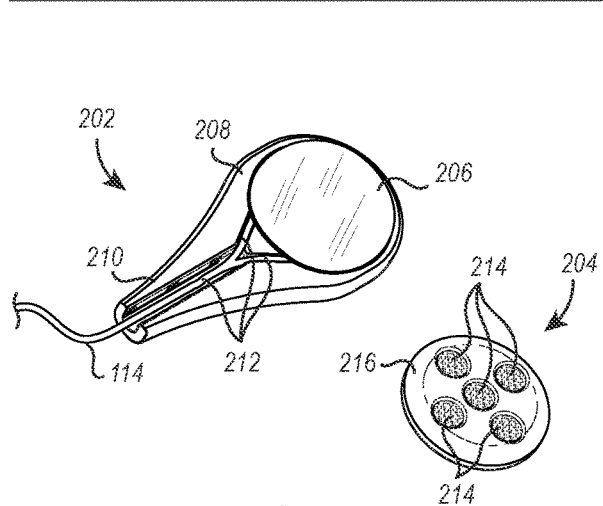
FIG. 9B illustrates various views of the return conductor illustrated in FIG. 9A.

As shown in FIG. 9A, in at least one embodiment, a return conductor 202 may be magnetically coupled to the return electrode 180 via an opposing magnetic element 204 disposed on an opposing side of the return electrode 180. One or more magnets may be disposed within both the return conductor 202 and the magnetic element 204 to secure the return conductor 202 to a surface of the return electrode 180. As illustrated in FIG. 9B, the return conductor 202 includes a conductive plate 206 disposed on a lower surface 208 of the return conductor 202. A casing 210 may include one or more channels 212 through which wires from the return cable 114 may pass to contact the conductive plate 206.

The casing 210 may also include recessed features behind the conductive plate 206 for housing one or more magnets. As noted above, the magnets disposed within the return conductor 202 attract the magnets 214 disposed within a casing 216 of the magnetic element 204 to secure the return conductor 202 to the return electrode 180. The number, shape, and arrangement of magnets 214 within the magnetic element 204 and return conductor 202 may vary in different embodiments. The strength of attraction between the magnets in the return conductor 202 and the magnetic element 204 may determine how securely the return conductor 202 maintains a connection with the return electrode 180.

In addition, the strength of the magnetic attraction between the return conductor 202 and magnetic element 204 may decrease the distance between the conductive plate 206 and the conductive element 184 within the return electrode 180. For example, as noted above, the pads 186, 188 surrounding the conductive element 184 may be compressible so that a strong magnetic attraction between the return conductor 202 and magnetic element 204 cause the pads 186, 188 to compress, bringing the conductive plate 206 closer to the conductive element 184. In this way, the magnets 214 may be selected and arranged within the return conductor 202 and the magnetic element 204 to optimize the distance between the conductive plate 206 and conductive element 184 based on the material properties and dimensions of the pads 186, 188 surrounding the conductive element 184.

Figure 9C:
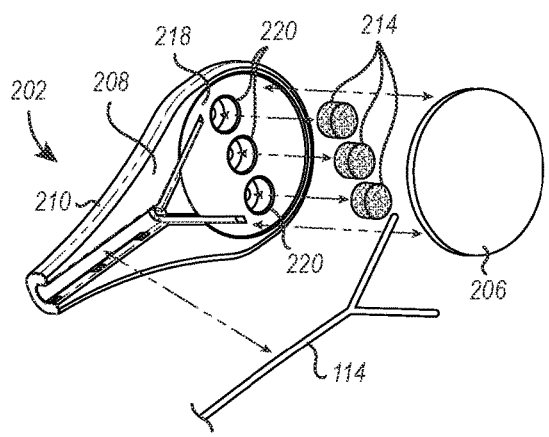
FIG. 9C illustrates an exploded view of one element of the return conductor illustrated in FIG. 9B.

FIG. 9C illustrates an exploded view of the return conductor 202, including the casing 210, magnets 214, conductive plate 206, and return cable 114. As seen, in at least one embodiment, the casing 210 of the return conductor 202 may comprise a recessed area 218 formed on a lower side 208 of the casing 210 in which the conductive plate 206 may be disposed. In such a configuration, the conductive plate 206 may be disposed such that direct contact is made between the conductive plate 206 and the return conductor 202. In at least one embodiment, the conductive plate 206 may be disposed within the casing 210 and thus separated from the return electrode 180 by the material of the casing 210.

In addition, in at least one embodiment, the casing 210 includes one or more recessed portions 220 configured to house one or more magnets 214. The arrangement, size, and number of recesses 220, as well as corresponding magnets 214, may vary in one or more other embodiments, so long as the magnets 214 disposed within the casing 210 of the return conductor 202 align sufficiently with the magnets 214 of the magnetic element 204 to secure the return conductor 202 to the return electrode 180.

Figure 9D:
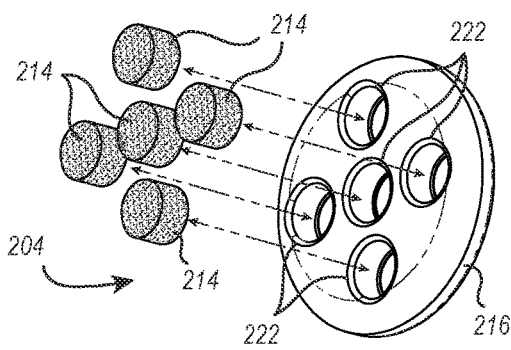
FIG. 9D illustrates an exploded view of another element of the return conductor illustrated in FIG. 9B.

Along these lines, FIG. 9D illustrates an exploded view of the magnetic element 204, according to an embodiment of the present disclosure. As shown, the magnetic element 204 includes a casing 216 having one or more recessed portions 222 configured to house magnets 214. Similar to the magnets 214 and recessed portions 220 of the return conductor 202 described above, the magnets 214 and recessed portions 222 of the magnetic element 204 may vary in size, shape, and arrangement so long as they sufficiently align with the magnets of the return conductor 202 to secure the return conductor 202 to the return electrode 180.

In addition, one of ordinary skill in the art will appreciate that one set of magnets 214, either those of the return conductor 202 those of the magnetic element 204 may alternatively comprise a ferrous material, rather than magnetic material, which would be attracted by opposing magnets 214 in the return conductor 202 and/or magnetic element 204.

In addition, the size, shape, materials, and configuration of the casing 210 of the return conductor 202 may vary in one or more other embodiments, so long as the return conductor 202 is magnetically attracted to the magnetic element 204 sufficiently to form a capacitive connection between the conductive element 184 inside the return electrode 180 and the conductive plate 206 to pass current into the return cable 114. For example, in at least one embodiment, the overall shape of the casing 210 may be rectangular, triangular, polygonal, or otherwise irregularly shaped. Likewise, the conductor plate 206 may be comprised of any suitable conducting material and be rectangular, triangular, polygonal, or otherwise irregularly shaped.

In addition, the conductive plate 206 may form a contact area as small as ½-square inch to as large as the return conductor 202 itself. Advantageously, in the embodiments of magnetically secured return conductors 202 described herein, the return conductor 202 may be placed anywhere on the return electrode 180 so long as the return conductor 202 and magnetic element 204 directly oppose one another on opposite sides of the return electrode 180. As such, a medical professional preparing for surgery may position the return conductor 202 on a portion of the return electrode 180 that is less likely to disrupt the operation being performed or contact the patient laying on the return electrode 180.

In at least one embodiment, the return conductor 202 may be placed on the top surface of the return electrode 180 with the opposing magnetic element 204 disposed on the bottom surface thereof. Alternatively, the return conductor 202 can be placed on the bottom surface of the return electrode 180 with the magnetic element 204 on the top surface thereof. While FIG. 9A illustrates the return conductor 202 placed near an edge of the return electrode 180, the return conductor can be placed at a location anywhere on the return electrode 180.

In addition, the return conductor 202 may be placed on the return electrode 180 such that the position of the return cable 114 extending therefrom does not get in the way of other devices or medical personnel during an operation. In this way, the magnetically secured return conductor 202 improves operating room integration. Additionally, the capacitive connection between the return conductor 202 and conductive element 184 can still operate under wet conditions, such as when fluids are present between the return conductor 202 and return electrode 180 during, thus reducing the risk of short-circuiting the electrosurgical system 101 and potentially harming the patient and medical personnel during use.

In particular, in embodiments including a conductive plate 206 disposed inside the casing 210 of the return conductor 202, or in embodiments with conductive plates 206 otherwise coated with a non-conductive material, the conductive plate 206 does not come into contact with fluid that may be present between the return conductor 202 and return electrode 180. In this way, no electrical/conductive elements are exposed, either from the return electrode 180 or conductor 202, to be corroded or damaged during use, further decreasing the risk of short-circuits and/or injury.

The capacitive connection between the return conductor 202 and conductive element 184 of the return electrode 180 thus provides increased safety and adaptability over common electrical plugs or other hard-wired connections between typical return electrodes and return cables currently known in the art.

In other embodiments, one or more magnetic elements 204 or magnets may be incorporated into the return electrode 180. For instance, one or more magnetic elements 204 or magnets may be secured in place between the pads 186, 188 and/or between the conductive element 184 and one or both of the pads 186, 188. In some embodiments, a magnetic element 204 or magnet may be secured within the return electrode 180 near one or more corners thereof and/or at one or more locations along one or more sides thereof. The return electrode 180 may include a visual indicator to identify the location(s) of the one or more magnetic elements 204 or magnets. In some embodiments, the return conductor 202 may be connected to the return electrode 180 by positioning the return conductor 202 in close proximity to at least one of the magnetic elements 204 or magnets incorporated into the return electrode 180.

Regardless of whether the magnetic element(s) 204 or magnetics are selectively attachable to the return electrode 180 (as shown in FIG. 9A) or incorporated into the return electrode 180 as noted above, attention should be paid to the orientation of the magnetic poles of the magnets in the return conductor 202 and the magnetic element(s) 204. For instance, assuring that opposing poles of the magnetics in the return conductor 202 and the magnetic element(s) 204 face one another can help ensure that a secure connection therebetween can be made (e.g., without the return conductor 202 slipping to one side of the magnetic element 204). Additionally, or alternatively, predetermined placement (including pole orientation) of the magnetics in the return conductor 202 and the magnetic element(s) 204 may allow the return conductor 202 to spin or rotate around a predefined point without becoming disconnected from the magnetic element(s) 204. This can allow for greater flexibility in the direction the return cable 114 extends away from the return electrode 180.

Figure 10A:
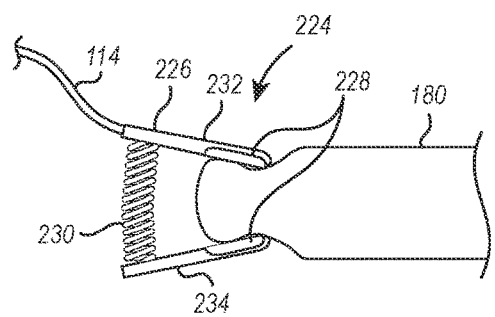
FIG. 10A illustrates an embodiment of a return conductor forming a capacitive connection with a return electrode, according to the present disclosure.

In addition to the magnetically secured return conductor 202 described herein, one or more other embodiments of the present disclosure may include other types of securement means that form a capacitive connection between the conductive element 184 within the return electrode 180 and the return conductor 202. For example, in at least one embodiment, as shown in FIG. 10A, a return conductor 224 includes a spring-biased clip 226 that secures one or more conductive plates 228 to the return electrode 180.

In general, in such an embodiment, a spring 230 interacts with two or more opposing clip members 232, 234 to bias those two members 232, 234 together around an edge of the return electrode 180. The biasing force of the spring 230 is strong enough to secure the clip 226 to the return electrode 180. Also, as shown in FIG. 10A, at least one of the clip members 232, 234 includes a conductor plate 228 on an inner surface of the clip member 232 that is pressed against the return electrode 180 during use, thus bringing the conductor plate 228 into close proximity with the conductive element 184 inside the return electrode 180. In at least one embodiment, both clip members 232, 234 include one or more conductive plates 228 disposed thereon.

Figure 10B:
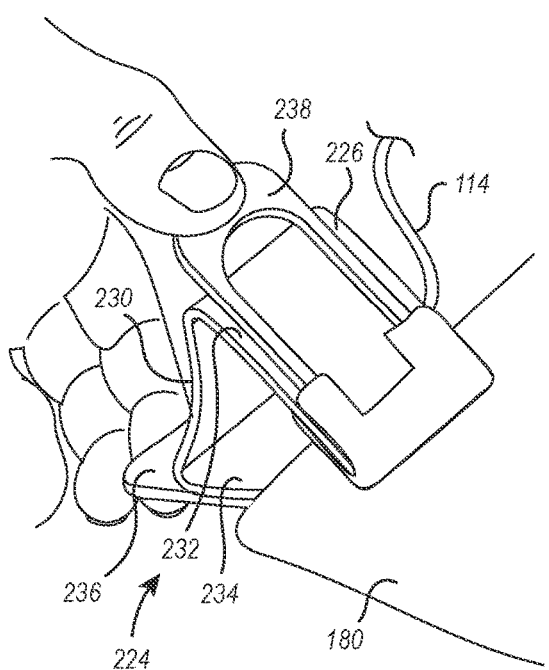
FIG. 10B illustrates an embodiment of a return conductor forming a capacitive connection with a return electrode, according to the present disclosure.

In at least one embodiment, the return cable 114 may be electrically connected to the one or more conductive plates 118 either directly or through the clip members 232, 234. FIG. 10B illustrates a perspective view of an embodiment of a return conductor 224 including a spring biased clip 226. In the illustrated embodiment of FIG. 10B, the spring biased clip 226 may take the form similar in functionality to a binder style paper clip so that a user can manipulate two or more handles 236, 238, each connected to a clip member 232, 234, to oppose the spring 230 while opening the clip 226 or release the clip members 232, 234 to be biased together during use. In this way, a medical professional can remove and reattach the return conductor 224 as needed.

The return conductor 224 may be clipped anywhere around the edge of the return electrode 180, either prior to or during an operation as needed. The extent to which the conductive plates 228 extend over the return electrode 180 depend on the length of the clip members 232, 234 to which the conductive plates 228 are attached.

Figure 11:
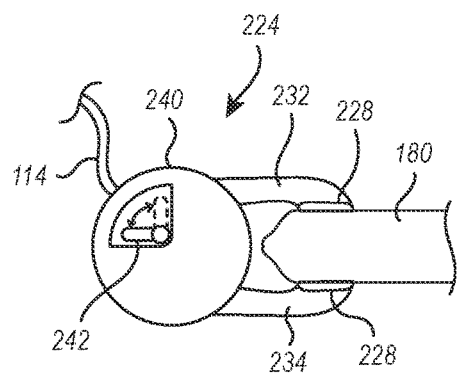
FIG. 11 illustrates an embodiment of a return conductor forming a capacitive connection with a return electrode, according to the present disclosure.

Alternatively, or additionally, in at least one embodiment, such as that shown in FIG. 11, the return conductor 224 includes a ratchet mechanism 240 that maintains a firm grip of the clip members 232, 234 around an edge of the return electrode 180, thus ensuring a proper connection between the conductive plates 228 and a conductive element inside the return electrode 180. In at least one embodiment, the ratchet mechanism 240 includes a switch 242 that operates to change the directionality of the ratchet mechanism 240. Using the switch, a user can clamp the clip members 232, 234 down around the return electrode 180 or release the clip members 232, 234 to release the return conductor 224.

Figure 12:
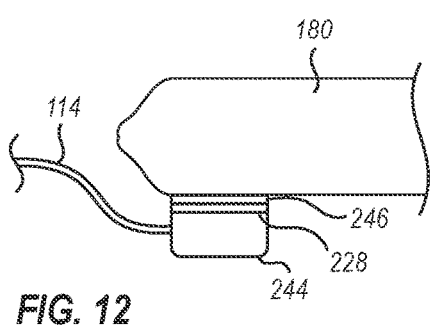
FIG. 12 illustrates an embodiment of a return conductor forming a capacitive connection with a return electrode, according to the present disclosure.

In at least one embodiment, as illustrated in FIG. 12, a return conductor 244 may include an adhesive layer 246 disposed between the conductive plate 228, or other material layer of the return conductor 244, and the return electrode 180. In such an embodiment, the return conductor 244 may be adhered anywhere on the outer surface of the return electrode 180, either on top or bottom, to place the conductive plate 228 in close enough proximity to a conductive element inside the return electrode 180 to form a capacitive connection therebetween.

In at least one embodiment, the adhesive layer 246 comprises a removable adhesive, such as a pressure sensitive adhesive, or friction adhesive such as a silicone material or the like. In at least one embodiment, the adhesive layer 246 may enable a removable and reusable connection between the return conductor 244 and the return electrode 180 such that the position of the connection therebetween can be selected prior to, or during, an operation as needed based on the position of the return electrode 180 and power source 100 within a room and/or based on the size and position of the patient on the return electrode 180.

Figure 13A:
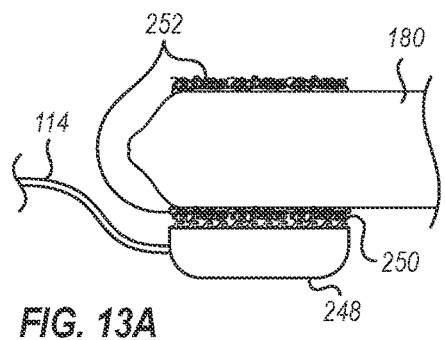
FIG. 13A illustrates an embodiment of a return conductor forming a capacitive connection with a return electrode, according to the present disclosure.

In at least one embodiment, as illustrated in FIG. 13A, a return electrode 180 may comprise a layer of hook-and-loop material 250 secured thereto that can be removably secured to an opposing, compatible portion 252 of hook-and-loop material secured to a surface of the return electrode 180. In this way, the return conductor 248 can be secured and removed from various portions of the return electrode 180, either a top portion, bottom portion, edge portion, or otherwise, before or during an operation, to create a capacitive connection between the return electrode 180 and the return cable 114.

Figure 13B:
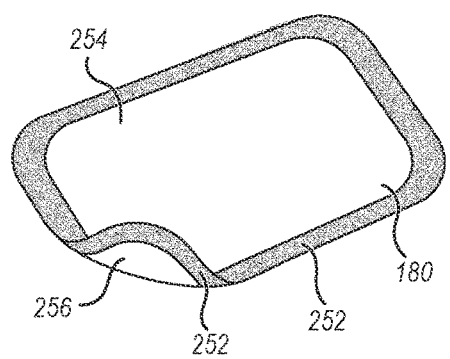
FIG. 13B illustrates an embodiment of the return electrode illustrated in FIG. 13A.

Accordingly, the position of the capacitive connection between such an embodiment of the return conductor 248 and the return electrode 180 depends on the placement of the opposing portion(s) 252 of the hook-and-loop material secured to the return electrode 180. For example, FIG. 13B illustrates an embodiment of a return electrode 180 having portions 252 of hook-and-loop material around the perimeter edges of both the top surface 254 and bottom surface 256. In at least one embodiment, only the top surface 254 or only the bottom surface 256 includes portions 252 of hook-and-loop material. In at least one embodiment, one or more portions 252 may be more centrally disposed on the top or bottom surface 254, 256 of the return electrode 180.

Figure 13C:
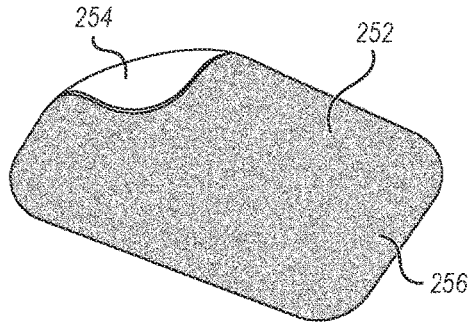
FIG. 13C illustrates an embodiment of a return electrode, according to the present disclosure.

In at least one embodiment, as illustrated in FIG. 13C, the portion 252 of hook-and-loop material may cover the entire bottom surface 256 of the return electrode 180 while the top surface 254 is completely free of hook-and-loop portions. In such an embodiment, the return conductor 248 may be placed anywhere beneath the return electrode 180, between the return electrode 180 and an operating table, to form the capacitive connection therebetween. One will appreciate that, while not all combinations and possible configurations of hook-and-loop portions 252 disposed on the return electrode 180 can be illustrated or described herein, the hook-and-loop portions 252 of the return electrode 180 can be strategically placed anywhere on the surface of the return electrode 180 to effectuate a capacitive connection between the return electrode 180 and the embodiment of the return conductor 248 illustrated in FIG. 13A.

Figure 14A:
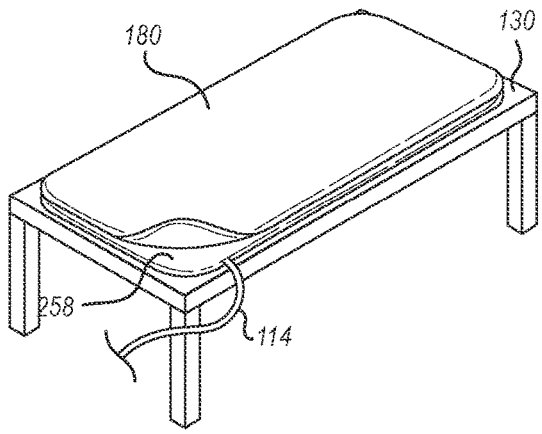
FIG. 14A illustrates an embodiment of a return conductor disposed between a return electrode and an operating table, according to the present disclosure.

In at least one embodiment, as shown in FIG. 14A, a return conductor 258 may comprise a conductive plate or pad that extends underneath the entirety of the return electrode 180 to form a capacitive connection therebetween. In the illustrated embodiment, the return conductor 258 has the same surface area as the return electrode 180. In such an embodiment, no connection features may be required as the weight of a patient or just the weight of the return electrode 180 itself secures the return conductor 258 in place between the table 130 and the return electrode 180. In at least one embodiment, the return conductor 258 may comprise one or more padded layers to form a pressure pad or similar pad for patient weight distribution and comfort.

Figure 14B:
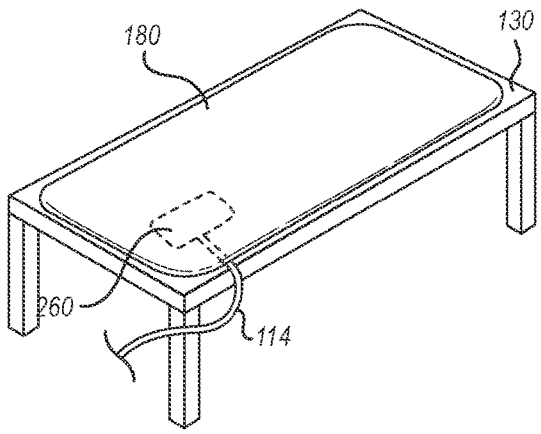
FIG. 14B illustrates an embodiment of a return conductor disposed between a return electrode and an operating table, according to the present disclosure.

Alternatively, as seen in FIG. 14B, the same type of capacitive connection can be made with a pad or plate 260 (shown indicated in dotted lines underneath the return electrode 180) that is smaller in area than the return electrode 180. In such an embodiment, the return conductor 260 can be placed anywhere underneath the return electrode 180 and held in place by the weight of the return electrode 180 and/or the patient. In at least one embodiment, the surface area of the return conductor 258, 260 is larger than the surface area of the return electrode 180.

Figure 15:
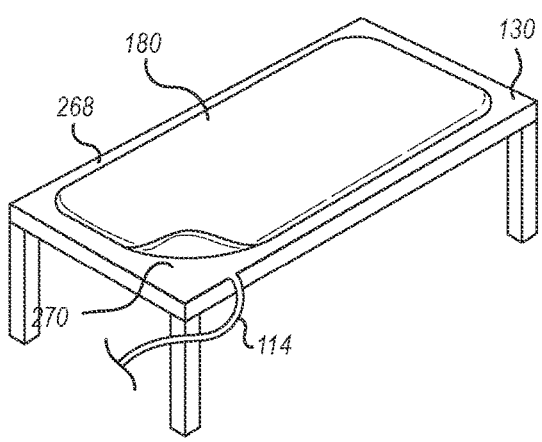
FIG. 15 illustrates an embodiment of a return conductor formed with an operating table and a return electrode placed thereon, according to the present disclosure.

In at least one embodiment, all or a portion of the top surface 268 of the operating table 130 may comprise a return conductor 270, as illustrated in FIG. 15. In at least one embodiment, the return conductor 270 may be integrally formed with the top surface 268 of the table 130 or formed to be the top surface 268 of the table 130. In such an embodiment, the return cable 114 may be connected directly to the top surface 268 of the table 130, through which current induced by the return electrode 180 passes.

Figure 16A:
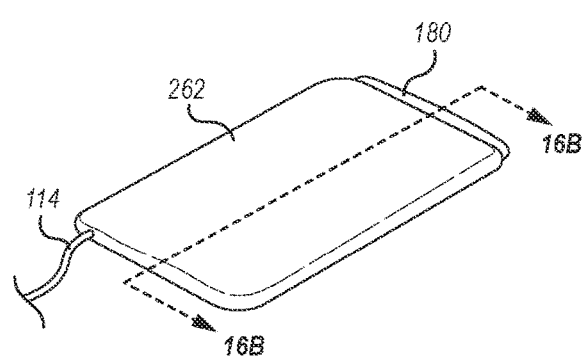
FIG. 16A illustrates an embodiment of a return conductor forming a capacitive connection with a return electrode, according to the present disclosure.

In at least one embodiment, as shown in FIG. 16A, a return conductor 262 may include an envelope into which the return electrode 180 is inserted. The return electrode 180 may be fully or partially inserted into the return conductor 262 and the envelope of the return conductor 262 may be sized to either fully or partially envelop the return electrode 180.

Figure 16B:
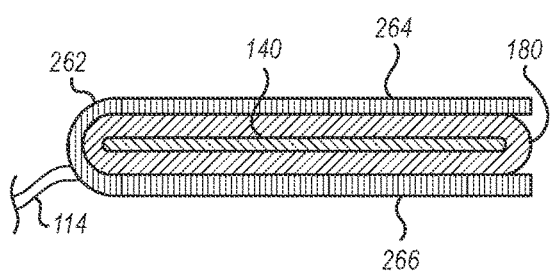
FIG. 16B illustrates a cross-sectional view thereof.

Along these lines, FIG. 16B illustrates a cross-sectional view of the return electrode 180 and return conductor 262 taken along the line 15 indicated in FIG. 16A. From the cross-sectional view of FIG. 16B the return conductor is shown to include an upper layer 264 and a lower layer 266 with the return electrode 180 inserted substantially fully therebetween. In at least one embodiment, not shown here, the return conductor 262 may include a cover or other closing portion to cover any exposed portion of the return electrode 180 so that the return electrode 180 is completely enveloped by the return conductor 262.

In at least one embodiment, the lower layer 266 of the return conductor 262 comprises a conductive plate. The lower layer 266 may thus form a capacitive connection between the conductive element 140 within the return electrode 180 and the return cable 114 due to the proximity of the lower layer 166 and the conductive element 140, as discussed above with reference to other embodiments. The lower layer 266 may also include one or more other padded elements or layers. The upper layer 264 may exhibit waterproof or water-resistant characteristics to shield the return electrode 180 from fluids.

Figure 17A:
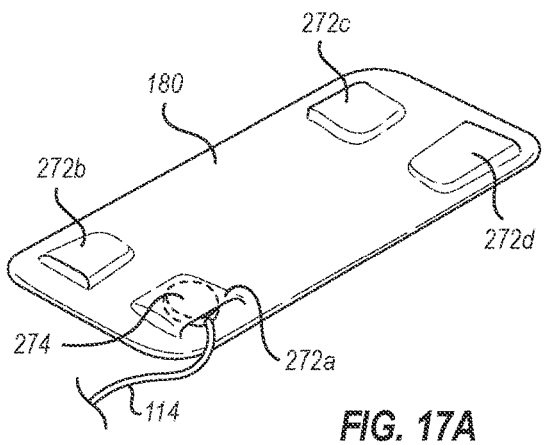
FIG. 17A illustrates an embodiment of a return electrode and a return conductor secured thereto, according to the present disclosure.
Figure 17B:
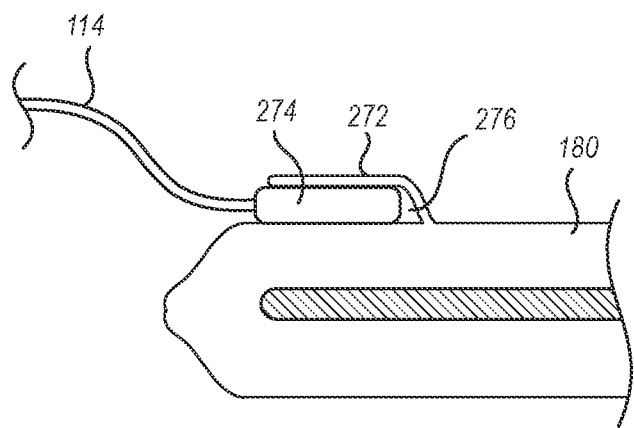
FIG. 17B illustrates a partial cross-sectional view thereof.

In at least one embodiment, as shown in FIG. 17A, the return electrode 180 may comprise one or more pockets 272a-d into which a return conductor 274 may be inserted, such as that shown in dotted lines inserted into pocket 272a. The pockets 272a-d may be arranged in any configuration or position on the top or bottom surfaces of the return electrode 180 to accommodate the return conductor 274 in a number of convenient locations. Various embodiments of return electrodes 180 may include more or less than the four pockets 272a-d shown in FIG. 17A. Along these lines, FIG. 17B illustrates a cross-sectional view of the return conductor 274 inserted into a pocket 272. The pocket 272 may include any number of configurations of material extending above or below the return electrode 180 that forms an inner space 276 into which the return conductor 274 may be inserted. The pocket 272 thus holds the return conductor 274 against the return electrode 180 to establish a capacitive connection therebetween.

In all embodiments of return electrodes and return conductors described herein, the size and shape of the return conductors and/or corresponding conductive plates disposed may vary. For example, in at least one embodiment, a return conductor or conductive plate thereof may be as small as ½-inch by ½-inch (in the case of a rectangular shape). Alternatively, in at least one embodiment, a return conductor or conductive plate thereof may be as large or larger than the return electrode to which it is connected.

Also, as noted above, the various material layers separating the conductive element 140, 184 of the return electrode 180 and the conductive plate(s) 228 of the various return conductors, be they padded layers, conductive layers, adhesive layers, hook-and-loop layers, return conductor casing layers, or the like, may be formed to specific thicknesses and from specific materials to accommodate specific electrical frequencies produced by the electrical power generator 100 and used by the hand-held surgical electrode 110. The thicknesses and materials of the various layers may be selected to avoid unwanted filtering of frequencies used during an operation and to effectuate successful capacitive connections between the conductive element 140, 184 of the return electrodes and the conductive plates 206, 228 of the return conductors.

The various embodiments of return conductors and/or return cables described herein may include one or more switching features that communicate with the electrical power generator 100. For example, in at least one embodiment, a return conductor (as seen throughout the figures) includes a switch that closes the electrical circuit of the electrosurgical systems described herein when the return electrode is placed on or around the return electrode 132, 180.

For example, in at least one embodiment, the return conductors of the present disclosure may include a reed switch disposed within the return conductor or return cable 114 and a magnet disposed within the return electrode 132, 180. In such an embodiment, the magnetic field produced by the magnet in the return electrode 132, 180 causes metal contacts within the reed switch to contact one another, thus activating the electrosurgical system 101 (as seen in FIG. 2).

In at least one example, the return conductors and/or return cables 114 of the present disclosure include one or more mechanical switches, such as a push switch or other mechanical switch, to activate the electrosurgical system 101 when the return conductors of the present disclosure are secured to the return electrode 132, 180 during use. Other switches commonly known and used in the art are also contemplated and may be used to perform substantially the same function as the reed switch and mechanical switch described above.

In addition, the various embodiments and elements of electrosurgical systems described herein are not necessarily exclusive of one another. Rather, some or all of the features described in each embodiment and/or element of electrosurgical systems described herein may be combined together with features and/or elements of other embodiments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical system, comprising:
a return electrode comprising a conductive element completely encompassed by one or more non-conductive or insulative pads, the return electrode being configured to draw electrical current from a surgical electrode; and
a return conductor configured for forming a capacitive electrical connection with the conductive element, the return conductor being configured to carry the electrical current from the return electrode to an electrical power generator or a common ground,
wherein the return electrode is devoid of an external electric plug.

2. The electrosurgical system of claim 1, wherein both the return electrode and the return conductor comprise an attachment feature configured to selectively secure the return conductor to the return electrode.

3. The electrosurgical system of claim 2, wherein the attachment features comprise mating hook-and-loop materials.

4. The electrosurgical system of claim 3, wherein the hook-and-loop material on the return electrode extends around at least a portion of a perimeter thereof.

5. The electrosurgical system of claim 3, wherein the hook-and-loop material on the return electrode comprises a hook-and-loop material on a first side of the return electrode and a hook-and-loop material on a second side of the return electrode.

6. The electrosurgical system of claim 3, wherein the hook-and-loop material on the return electrode covers substantially an entire surface thereof.

7. The electrosurgical system of claim 1, wherein the return conductor is configured to be removably secured to the return electrode.

8. The electrosurgical system of claim 7, wherein:
the return conductor comprises a layer of hook-and-loop material disposed thereon;
the return electrode comprises a first portion of hook-and-loop material secured thereto; and
the first portion of hook-and-loop material secured to the surface of the return electrode is compatible with the layer of hook-and-loop material disposed on the return conductor such that when brought together during use, the layer and first portion of hook-and-loop material removably secures the return conductor to the return electrode.

9. The electrosurgical system of claim 8, wherein:
the return electrode further comprises a second portion of hook-and-loop material secured thereto;
the first portion of hook-and-loop material is secured around a perimeter edge of a top surface of the return electrode; and
the second portion of hook-and-loop material is secured around a perimeter edge of a bottom surface of the return electrode.

10. The electrosurgical system of claim 8, wherein the first portion of hook-and-loop material entirely covers a bottom surface of the return electrode.

11. An electrosurgical system, comprising:
an electrical power generator;
a surgical electrode electrically connectable to the electrical power generator;
a return electrode comprising a conductive element completely encompassed by one or more non-conductive or insulative pads, the return electrode being configured to draw electrical current from the surgical electrode, the return electrode is devoid of an external electric plug;
a return cable configured to carry electrical current from the return electrode to the electrical power generator or a common ground; and
a return conductor configured to form a capacitive connection between the return cable and the conductive element of the return electrode.

12. The electrosurgical system of claim 11, wherein at least one of the return electrode or the return conductor comprises an attachment feature configured to selectively secure the return conductor to the return electrode to maintain the capacitive connection therebtween.

13. The electrosurgical system of claim 12, wherein both the return electrode and the return conductor comprise an attachment feature configured to selectively secure the return conductor to the return electrode.

14. The electrosurgical system of claim 13, wherein the attachment features comprise a first layer of hook-and-loop materials on the return electrode and a mating second layer of hook-and-loop on the return conductor.

15. The electrosurgical system of claim 14, wherein the first layer of hook-and-loop material on the return electrode extends around at least a portion of a perimeter thereof.

16. The electrosurgical system of claim 14, wherein the first layer of hook-and-loop material on the return electrode comprises a hook-and-loop material on a first side of the return electrode and a hook-and-loop material on a second side of the return electrode.

17. The electrosurgical system of claim 13, wherein the first layer of hook-and-loop material on the return electrode covers substantially an entire surface thereof.

18. The electrosurgical system of claim 17, wherein the return conductor is integrally formed with a top surface of an operating table.

19. The electrosurgical system of claim 11, wherein the return conductor comprises an envelope into which at least a portion of the return electrode is inserted during use.

20. The electrosurgical system of claim 19, the envelope comprising:
an upper layer that is water resistant.

21. The electrosurgical system of claim 11, wherein the return electrode comprises one or more pockets, wherein the return conductor is insertable into at least one of the one or more pockets such that the one or more pockets secures the return conductor to the return electrode to form the capacitive connection during use.

22. An electrosurgical system, comprising:
a return electrode being configured to draw electrical current from a surgical electrode, comprising:
an upper pad;
a lower pad; and
a conductive element disposed between the upper and lower pads, wherein the upper and lower pads extend beyond an outer perimeter of the conductive element such that the conductive element is completely encompassed by the pads, the return electrode is devoid of an external electric plug;
a return conductor comprising a conductive plate, the return conductor being configured to be removably secured to the return electrode such that the conductive plate is capacitively connected to the conductive element of the return electrode to carry the electrical current from the return electrode to an electrical power generator or a common ground; and
one or more attachment features configured to selectively secure the return conductor to the return electrode in a manner that maintains the capacitive connection between the return conductor and the return electrode.

23. The electrosurgical system of claim 22, wherein the upper pad and the lower pad are joined together at a pad juncture around an outer perimeter of the conductive element.

* * * * *